(12) United States Patent
Couderc et al.

(10) Patent No.: US 10,501,391 B2
(45) Date of Patent: Dec. 10, 2019

(54) PROCESS FOR PRODUCING BUTADIENE FROM ETHANOL, COMPRISING PURIFICATION OF A BUTADIENE-LOADED EFFLUENT BY EXTRACTIVE DISTILLATION

(71) Applicants: IFP Energies Nouvelles, Rueil-Malmaison (FR); Compagnie Generale des Establissements Michelin, Clermont-Ferrand (FR)

(72) Inventors: Sophie Couderc, Neuilly sur Seine (FR); Rejane Dastillung, Lyons (FR); Olivier Thinon, Roanne (FR)

(73) Assignees: IFP Energies Nouvelles, Rueil-Malmaison (FR); Compagnie Generale des Etablissements Michelin, Clermont-Ferrand (FR)

( * ) Notice: Subject to any disclaimer, the term of this patent is extended or adjusted under 35 U.S.C. 154(b) by 0 days.

(21) Appl. No.: 16/314,004

(22) PCT Filed: Jun. 26, 2017

(86) PCT No.: PCT/EP2017/065741
§ 371 (c)(1),
(2) Date: Dec. 28, 2018

(87) PCT Pub. No.: WO2018/001981
PCT Pub. Date: Jan. 4, 2018

(65) Prior Publication Data
US 2019/0169095 A1    Jun. 6, 2019

(30) Foreign Application Priority Data
Jun. 29, 2016 (FR) .................. 16 56050

(51) Int. Cl.
| | | |
|---|---|---|
| C07C 1/20 | (2006.01) |
| C07C 11/167 | (2006.01) |
| C07C 7/00 | (2006.01) |
| C07C 7/04 | (2006.01) |
| C07C 7/08 | (2006.01) |
| C07C 7/11 | (2006.01) |
| C07C 1/24 | (2006.01) |

(52) U.S. Cl.
CPC .............. *C07C 11/167* (2013.01); *C07C 1/20* (2013.01); *C07C 1/24* (2013.01); *C07C 7/005* (2013.01); *C07C 7/04* (2013.01); *C07C 7/08* (2013.01); *C07C 7/11* (2013.01)

(58) Field of Classification Search
CPC .......... C07C 11/167; C07C 7/04; C07C 7/08; C07C 7/005; C07C 7/11; C07C 7/10; C07C 45/002; C07C 1/24; B01D 3/143; B01D 3/4211; B01D 11/04; B01D 3/009; B01D 3/14; B01D 61/362; B01D 2256/24; B01D 2257/7022; B01D 3/141; B01D 3/148; B01D 3/40; B01D 3/42; B01D 5/006
See application file for complete search history.

(56) References Cited

U.S. PATENT DOCUMENTS

| | | | | |
|---|---|---|---|---|
| 2,403,742 A | * | 7/1946 | Murray ................. | C07C 1/2072 585/327 |
| 2,403,743 A | * | 7/1946 | Hitchcock ............. | C07C 1/2072 585/607 |
| 9,776,933 B2 | | 10/2017 | Dastillung et al. | |
| 2016/0376206 A1 | | 12/2016 | Dastillung et al. | |
| 2017/0291859 A1 | | 10/2017 | Dastillung et al. | |

FOREIGN PATENT DOCUMENTS

| | | |
|---|---|---|
| WO | 2015/079040 A1 | 6/2015 |
| WO | 2016/042095 A1 | 3/2016 |

OTHER PUBLICATIONS

International Search Report dated Sep. 6, 2017 issued in corresponding PCT/EP2017/065741 application (2 pages).

* cited by examiner

*Primary Examiner* — Sharon Pregler
(74) *Attorney, Agent, or Firm* — Millen White Zelano & Branigan, PC

(57) ABSTRACT

The invention relates to a process for producing butadiene from an ethanol feedstock, comprising a step of converting the ethanol into butadiene, a distillation step, a step of washing with water, a butadiene purification step comprising at least one section for separating the 1-butene by extractive distillation and a final distillation section fed with the topped butadiene distillate, separating at the top a purified butadiene effluent and at the bottom a butene residue, and an effluent treatment step.

13 Claims, 1 Drawing Sheet

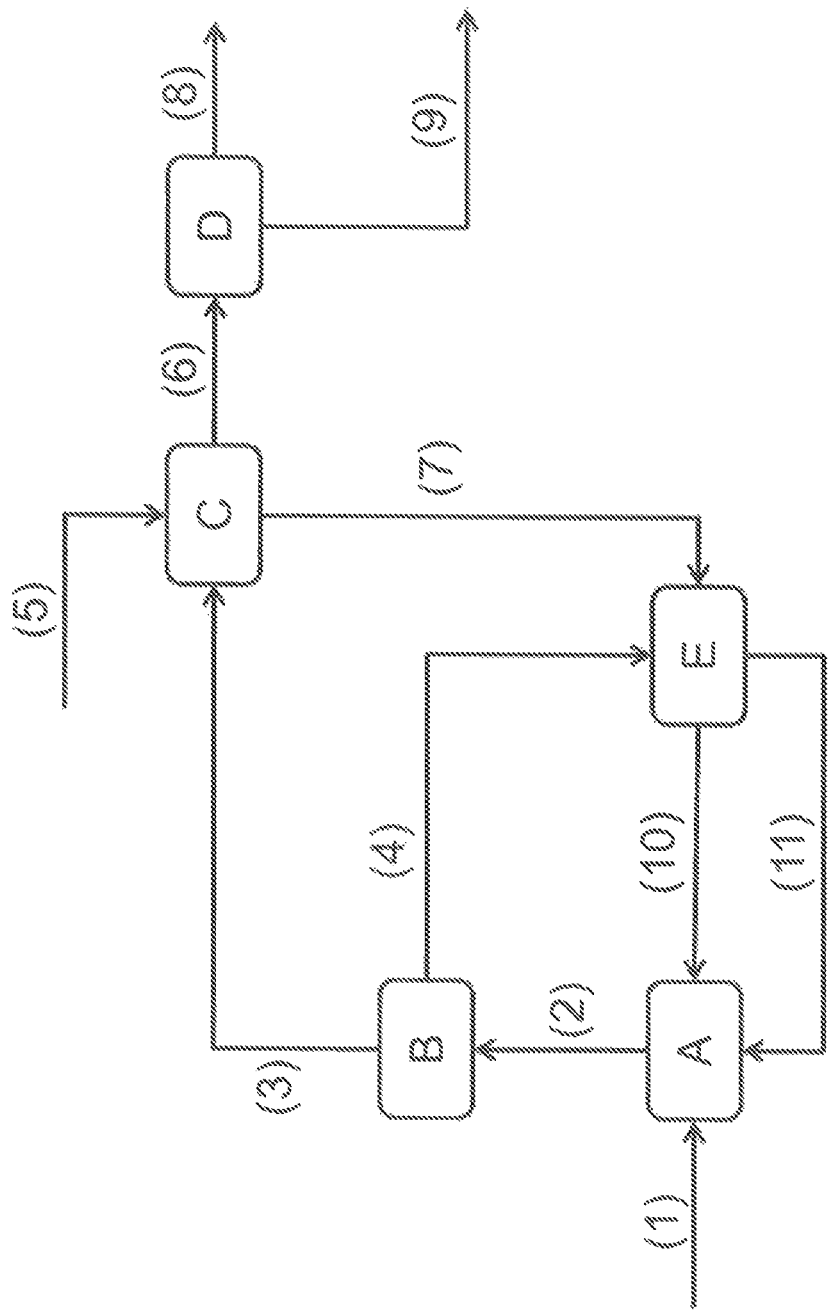

PROCESS FOR PRODUCING BUTADIENE FROM ETHANOL, COMPRISING PURIFICATION OF A BUTADIENE-LOADED EFFLUENT BY EXTRACTIVE DISTILLATION

TECHNICAL FIELD OF THE INVENTION

The invention relates to a process for producing butadiene from ethanol.

PRIOR ART

The process for producing 1,3-butadiene from ethanol, in one or two reaction steps, has a limited degree of conversion per step. This leads to substantial recycling, made complex by the large number of impurities co-produced with the 1,3-butadiene, the extraction of which compromises the overall yield of the process. Each loss in the individual operations, in particular in the numerous separation operations, is thus reflected by an overall loss within the process, which rapidly becomes economically unacceptable. These losses led to stop the exploitation of these processes at the end of the Second World War.

Among the impurities, mention may be made of hydrocarbons comprising from 1 to 16 carbon atoms, which may be saturated or unsaturated, or even aromatic, and also oxygenated products such as alcohols, phenols, aldehydes, ketones, acids, esters, ethers and acetals, which may be saturated or unsaturated, or even aromatic.

Under normal temperature and pressure conditions, the main gaseous byproducts that may be mentioned include hydrogen, carbon monoxide, carbon dioxide, $C_1$-$C_4$ alkanes and olefins and methyl ethyl ether, and the main liquid byproducts that may be mentioned include pentenes, pentadienes, diethyl ether, ethyl vinyl ether, hexenes, hexadienes, butanal, crotonaldehyde, ethyl acetate, diethyl acetal, butanol, hexanol and acetic acid.

Other byproducts are generated in tiny amounts. In the rest of the document, the term "brown oils" will be used to denote as a whole hundreds of oxygenated and hydrocarbon compounds produced in reaction sections, the boiling points of which are between that of ethanol and ranging up to 600° C. A particular feature of these brown oils is that they are soluble in ethanol, but insoluble in water. They are liable, whenever they are not diluted with a large excess of ethanol, to foul and clog equipment. Moreover, these brown oils cause problems in the distillation column which separates the water produced by the reaction and the unconverted ethanol. Specifically, these brown oils are soluble in the water-ethanol effluent feeding said distillation column, and insoluble in the residue essentially constituted of water. A phase separation thus takes place within this column, considerably reducing the separation efficiency. Brown oils are difficult to remove in the process due to the fact that they are constituted of hundreds of compounds with very different physicochemical properties. A fraction of these brown oils thus accumulates in the process, entailing a reduction in its efficiency after a few days and at best a few weeks of operation and necessitating periodic purging of certain streams. The loss of ethanol and acetaldehyde thereby occasioned degrades the overall yield of the process for a cost that would at the present time be prohibitive.

The purification of butadiene involves a combination of numerous individual operations, such as washes and simple and extractive distillations. The prior art teaches the use of extractive distillations using the solvent bis(2-chloroethyl) ether, or Chlorex, which is nowadays banned since it is highly toxic. It is important to note that the specifications for butadiene are nowadays extremely stringent, owing to the sensitivity of the butadiene polymerization catalysts. For example, the specification for acetaldehyde (intermediate reagent for producing butadiene) in butadiene has gone from 1000 ppm to less than 10 ppm at the present time. The publication "Synthetic rubber from alcohol", (A. Talalay, M. Magat, 1945) gives a general view of the processes developed up to the 1940s.

U.S. Pat. No. 2,409,250 describes the successive steps for the purification of butadiene (extraction, first purification and final purification of butadiene by super-fractionation). Butadiene is produced in a purity of 98.7%, but at the expense of a significant loss of yield. To limit this loss, the head products from the column for butadiene purification by super-fractionation are removed and partly recycled into the butadiene extraction step. This substantial recycling, in particular the recycling of the butene/butadiene stream in order to remove the uncondensable matter, entails overdimensioning of the equipment.

U.S. Pat. No. 1,948,777 describes in detail the final step of butadiene purification by extractive distillation using various solvents, including Chlorex. By limiting the loss of butadiene at the column head, i.e. a concentration of 0.2% of butadiene in the distillate, the butadiene purity obtained at the bottom is only 70%, whereas by seeking to obtain a purer butadiene at the bottom, i.e. 99%, the loss of butadiene at the top is much greater, with a butadiene concentration in the distillate of 30%. The production of a high-purity butadiene is thus achieved at the expense of a very great reduction in the overall yield of the unit.

WO 14199348 describes a method for obtaining butadiene from an effluent containing ethanol and optionally acetaldehyde on a catalyst based on a zeolite material. Ethanol conversions of greater than 95% and butadiene selectivities of between 20% and 48% are obtained. The patent mentions the production of oxygenated compounds such as diethyl ether, crotonaldehyde and ethyl acetate, which are separated from the butadiene by distillation, without giving any further details. No information is given regarding the management of the numerous other impurities that may be present or regarding the means for purifying the butadiene in order to meet the specifications required regarding its use in downstream processes.

The catalyst becomes deactivated in the course of its use, the consequence being a degradation in the selectivity towards butadiene and the production of a larger amount of impurities such as 1-butyne, 1,2-butadiene, n-butane and butenes. These impurities become partially or totally entrained with the butadiene in the steps for separating said butadiene from acetaldehyde and ethanol.

WO 2016/042096 and WO 2016/042095 describe a process for producing butadiene from an ethanol feedstock, in one and two reaction steps, respectively, with an arrangement of individual operations enabling the removal of the gaseous and liquid impurities while at the same time minimizing the loss of ethanol and acetaldehyde, thus improving the overall yield of the unit while reducing the overall flow of water required in the separation steps and obtaining a very pure butadiene. The final purification of the butadiene is performed by liquid-liquid extraction. However, specific impurities such as butynes may be produced in critical contents with regard to the specification for the butadiene product obtained via the process when the catalysts become deactivated. This problem is not addressed in said patents. Moreover, the proposed liquid-liquid extraction step requires pre-purification of the butadiene effluent to remove the light compounds, the residual water and oxygenated compounds such as acetaldehyde, ethanol or diethyl ether.

At the present time, the main source of butadiene is from oil. This butadiene is extracted from a $C_4$ fraction produced by vapour cracking of naphtha, containing between 35% and 60% by weight of butenes/butanes, between 30% and 60% by weight of butadiene, typically 0.5% to 2% by weight (sometimes more) of acetylenes, in particular vinylacetylene, and also a small amount of 1,2-butadiene (about 0.1% by weight) and light compounds such as propane and propylene. The extraction is performed by extractive distillation with a polar aprotic solvent, in a purity of greater than 99.5% by weight and a yield generally greater than 98% by weight.

Extractive distillations using N-methylpyrrolidone (NMP), dimethylformamide (DMF) and acetonitrile (ACN) are the ones most used and the most widespread as solvents.

Extractive distillation applied to the $C_4$ fractions obtained from vapour cracking is an alternative, but its extrapolation to the butadiene effluents obtained from production processes starting with ethanol is not obvious on account of various compositions, namely a butadiene concentration of greater than 80% by weight and a concentration of butenes and butanes of less than 15% by weight, a globally lower content of acetylenes and the potential presence of oxygenated compounds such as acetaldehyde, diethyl ether (DEE) and water, and of alkynes produced with the gradual deactivation of the catalysts.

Objective and Advantage of the Invention

The invention relates to a process for producing butadiene from an ethanol feedstock comprising at least 80% by weight of ethanol, said process comprising:
a) a step for converting the ethanol into butadiene, comprising:
  a water-ethanol separation section fed with at least a fraction of said ethanol feedstock and with a fraction of the ethanol-water effluent obtained from step e) and producing an ethanol effluent and a purged water effluent;
  a reaction section fed with said ethanol effluent and operated at a pressure of between 0.1 and 1.0 MPa and at a temperature of between 200 and 500° C. in the presence of a catalyst and producing a reaction effluent;
b) a distillation step fed with the reaction effluent obtained from step a) and producing a polluted reagent residue and a butadiene distillate, operated at a pressure of between 0.1 and 1 MPa;
c) a step of washing with water comprising at least one gas-liquid washing section fed at the bottom with the butadiene distillate obtained from step b) and at the top with a stream of water, advantageously originating from outside said butadiene production process, and producing at the top a hydrated butadiene extract and at the bottom a spent water raffinate;
d) a butadiene purification step fed with the butadiene extract obtained from step c) and producing at least one light gas effluent and a purified butadiene effluent comprising at least:
  a section for separating the 1-butene by extractive distillation fed with said butadiene extract, which is advantageously compressed, and with a stream comprising a solvent, separating at the top a light gas effluent and, at the bottom a butadiene residue;
  a section for separating out the solvent by distillation fed with said butadiene residue, separating at the top a topped butadiene distillate and at the bottom a solvent residue;
  a final distillation section fed with the topped butadiene distillate, separating at the top a purified butadiene effluent and at the bottom a butene residue;
e) an effluent treatment step fed with the spent water raffinate obtained from step c) and with the polluted reagent residue obtained from step b) and producing at least one ethanol-acetaldehyde effluent, an ethanol-water effluent and one or more brown oil effluents.

The process according to the invention enables a significant energy saving with regard to the prior art. In particular, the absence of treatment of the vapour fraction of the reaction effluent by washing with a stream of ethanol followed by washing with water and the absence of loops for recycling the aqueous effluents of the process make it possible to reduce the circulation flows of ethanol and water in the effluent treatment sections and, as a result of this reduction, to relieve said sections.

The process according to the invention also makes it possible to produce a butadiene to the specifications, even when byproducts, in particular butynes, are generated in a larger amount due to the deactivation of the catalysts used in the reaction steps, with no loss of overall yield and with a maintained energy saving.

DETAILED DESCRIPTION OF THE INVENTION

Feedstock

The ethanol feedstock used in the process according to invention may originate from any fossil, plant or animal origin, and in particular from processes for producing ethanol from plant resources. Said feedstock comprises at least 80% by weight of ethanol, preferentially at least 90% by weight, and preferably at least 93% by weight. Very preferably, said ethanol feedstock meets the EN 15376 fuel ethanol specifications.

Step a) of Converting Ethanol into Butadiene

The process according to invention comprises a step a) of converting ethanol into butadiene.

Said step a) comprises a water-ethanol separation section fed with at least a fraction of said ethanol feedstock and with a fraction of the ethanol-water effluent obtained from step e) and producing an ethanol effluent and a purged water effluent.

The ethanol effluent obtained from said section is predominantly constituted of ethanol. The term "predominantly" means more than 80% by weight, preferably more than 84% by weight. In a non-limiting manner, the ethanol-rich effluent obtained from said section may contain impurities such as water, ethyl acetate, butanol and hexanol. The impurities other than water preferentially represent less than 10%, preferably less than 5% and even more preferentially less than 2% by weight of said effluent.

Said water-ethanol separation section advantageously operates by distillation. At least a fraction of said ethanol feedstock is then introduced into the top of said distillation, the effect of which is to facilitate the distillation of the ethanol in the presence of impurities, to reduce the reflux and to increase the ethanol concentration in the ethanol effluent feeding the reaction section and thus to lower the total flow rate of this effluent for the same flow rate of ethanol, which makes it possible to work with a reaction section of smaller volume than in the prior art, in which the ethanol feedstock is first used for dissolving the butadiene in the vapour effluent of the reaction section.

This use of the ethanol feedstock according to the prior art has the advantage of making it possible to extract the lightest compounds included in the effluent from the reaction section, these compounds being separated by successive washes with the ethanol feedstock and with a stream of water. In the process according to the invention, these light compounds remain with the butadiene up to the butadiene purification step, the consequence of which is to increase the size of the equipment and may, depending on the concentration of light compounds, impose the use of a pre-washing step or of cold groups at the top of the 1-butene separation sections so as to ensure the liquefaction of part of the distillate and to ensure reflux. This choice is thus, in principle, harmful to the performance of the process.

Now, the Applicant has realized that feeding of the ethanol feedstock into the top of a water-ethanol separation section in combination with a butadiene purification step performed by extractive distillation and which is more capable of managing the light compounds, despite the sending of the light compounds into the distillation step b) (which in principle has a negative impact since it is more energy-demanding), resulted overall in an improvement in the performance of the process according to the invention, in particular by improving the functioning of the water-ethanol separation section and by minimizing the ethanol-acetaldehyde reaction in all the sections in which ethanol and acetaldehyde are present (recycling loops).

In one embodiment of the invention, the ethanol effluent undergoes a purification step before being fed into the reaction section. The term "purification" means placing said effluent in contact with adsorbents, for instance active charcoal, silica, alumina or a functionalized polymeric resin. For example, an active charcoal makes it possible to remove the traces of butanol, methanol and hexanol.

Said step a) comprises a reaction section fed with said ethanol effluent and optionally part of said ethanol feedstock, and operated at a pressure of between 0.1 and 1.0 MPa, preferably between 0.1 and 0.5 MPa, even more preferably between 0.1 and 0.3 MPa and at a temperature of between 200 and 500° C. in the presence of a catalyst and producing a reaction effluent.

In a first particular arrangement of the process according to the invention, said reaction section comprises a reaction zone fed with said ethanol effluent and optionally with part of said ethanol feedstock, making it possible to convert the ethanol at least into butadiene. It is operated in the presence of any catalyst known to a person skilled in the art, for example a silica/magnesium oxide catalyst, at a temperature advantageously between 300 and 400° C., preferably between 320 and 370° C. and at a pressure advantageously between 0.1 and 0.5 MPa, preferably between 0.1 and 0.3 MPa.

In a second particular arrangement of the process according to the invention, said reaction section comprises two reaction zones, the first one, fed with a fraction of said ethanol effluent and optionally part of said ethanol feedstock, making it possible to convert the ethanol into acetaldehyde, and the second one fed with the effluent from the first reaction zone, with the residual fraction of said ethanol effluent and with a fraction of the ethanol-acetaldehyde effluent obtained from step e) and optionally with a part of said ethanol feedstock, making it possible to convert the mixture of ethanol and acetaldehyde at least into butadiene.

Advantageously, in this second arrangement, a gas-liquid separation means is used between the two reaction zones in order to separate the effluent from the first reaction zone into a gaseous effluent and a liquid effluent. The gaseous effluent, comprising hydrogen, may be treated in the same way as the hydrogen effluent according to the hydrogen treatment steps C1) and C2) described in WO 2016/042095. The liquid effluent feeds the second reaction zone.

In the second arrangement, said first reaction zone is operated in the presence of a catalyst comprising a copper oxide, or any other suitable catalyst well known to a person skilled in the art.

The ethanol/acetaldehyde mole ratio at the inlet of said second reaction zone is between 1 and 5, preferably between 1 and 3.5 and even more preferably between 2 and 3.5. Said second reaction zone is operated in the presence of a catalyst, advantageously a catalyst supported on silica chosen from the group constituted by catalysts comprising tantalum oxide, zirconium oxide or niobium oxide, preferentially comprising 2% tantalum oxide (see, for example, Corson, Jones, Welling, Hincbley, Stahly, Ind. Eng Chem. 1950, 42, 2, 359-373). Said second reaction zone is operated at a temperature of between 300 and 400° C., preferably between 320 and 370° C. and at a pressure of between 0.1 and 1.0 MPa, preferably between 0.1 and 0.5 MPa, preferably between 0.1 and 0.3 MPa.

The reaction effluent from said reaction zone in the first particular arrangement according to the invention, or from said second reaction zone in the second particular arrangement according to the invention, still comprises ethanol, and also numerous impurities produced with the butadiene, among which are hydrogen, ethylene, propylene, diethyl ether (DEE), ethyl acetate, butanol, hexanol, butenes, butynes, pentenes, pentadienes, hexenes, hexadienes, crotonaldehyde, butyraldehyde, diethyl acetal and acetic acid. It feeds the distillation step b).

Distillation Step b)

The process according to the invention comprises a distillation step b) fed with the reaction effluent obtained from step a) and producing a polluted reagent residue and a butadiene distillate.

The reaction effluent obtained from step a) feeds said distillation step b) so as to separate at the top a butadiene distillate comprising the majority of the butadiene, and at the bottom a polluted reagent residue. The term "the majority" means more than 80% by weight of the butadiene included in the feed of said distillation step, preferentially more than 90%, preferably more than 95%, even more preferably more than 98%, very preferably more than 99% and very advantageously more than 99.5% by weight of the butadiene included in said feed of said step.

This polluted reagent residue comprises ethanol and acetaldehyde, and also comprises water and byproducts formed in step a), for instance diethyl ether, ethyl acetate and brown oils. Said polluted reagent residue then feeds the effluent treatment step e). Said distillation step b) is operated at a pressure of between 0.1 and 1 MPa and preferably between 0.2 and 0.5 MPa.

The reaction effluent obtained from step a) advantageously undergoes a gas-liquid separation before feeding step b). This separation consists in cooling the reaction effluent obtained from step a) to a temperature of between 10 and 100° C., preferably between 25 and 80° C., to condense part of said reaction effluent and to obtain, in a gas/liquid separator, at least one liquid effluent and at least one vapour effluent. This section may advantageously be operated with several gas/liquid cooling and separation stages optionally with compression of the vapour effluents between two stages. The vapour effluent then feeds the distillation step b)

as reaction effluent obtained from step a). The liquid effluent feeds the effluent treatment step e).

Step c) of Washing with Water

The process according to the invention comprises a step c) of washing with water fed with a stream of water and with the butadiene distillate obtained from step b) and producing a hydrated butadiene extract and a spent water raffinate.

Step c) of washing with water comprises at least one gas-liquid washing section fed at the bottom with the butadiene distillate obtained from step b) and at the top with a stream of water, preferably originating from outside said butadiene production process, and producing at the top a hydrated butadiene extract and at the bottom a spent water raffinate.

Said spent water raffinate contains acetaldehyde and a small amount of butadiene, and feeds the effluent treatment step e).

The object of step c) is to remove the polar impurities, in particular the acetaldehyde which must not be present beyond a few ppm in the final butadiene. The butadiene distillate obtained from b) comprises the majority of the butadiene, but still contains many impurities, including a large amount of acetaldehyde which forms a substantial affinity with the butadiene and therefore cannot be completely removed by distillation during step b). Thus, the flow rate of said stream of water is adjusted to obtain the desired specification for acetaldehyde in the purified butadiene effluent obtained from step d). Step c) also makes it possible to recover all the residual polar impurities entrained in the butadiene distillate.

Said stream of water is advantageously cooled to a temperature below 25° C., preferably below 20° C., before feeding the gas-liquid washing section so as to perform the washing with a reduced amount of water. The feed temperature of said stream of water is chosen so as not to form hydrates with the butadiene and the light hydrocarbons still present in the butadiene distillate obtained from step b). The pressure of the washing column is determined so as to ensure that there is no condensation of the butadiene and so that it clearly remains in gaseous form. The pressure in this step is preferably between 0.1 and 1 MPa and even more preferably between 0.2 and 0.3 MPa.

Butadiene Purification Step d)

The process according to the invention comprises a butadiene purification step d) fed with the butadiene extract obtained from step c) and producing at least one light gas effluent and a purified butadiene effluent.

The hydrated butadiene extract obtained from step c) is advantageously compressed to a pressure of between 0.1 and 1.0 MPa, preferentially between 0.1 and 0.7 MPa and preferably between 0.2 and 0.5 MPa. The effect of this compression is mainly to reduce the volume flow of gas. It is not necessary to cool the butadiene extract at the end of its compression.

Said step d) is fed with the butadiene extract, advantageously compressed, obtained from step c). Said butadiene extract comprises at least 70% by weight, preferably at least 80% by weight of butadiene and also impurities, due in particular to the degradation of the selectivity towards butadiene in the reaction section, among which are traces of oxygenated impurities such as acetaldehyde, diethyl ether and water, and not more than 15% by weight of $C_4$ impurities such as butenes and butanes, hydrocarbons comprising at least 5 carbon atoms ($C_5^+$ hydrocarbons) and also light gases, in particular hydrogen, ethane, ethylene, propane and propylene.

Said step d) comprises a section for separating the 1-butene by extractive distillation fed with said butadiene extract, which is advantageously compressed, and with a stream comprising a solvent, and separating at the top a light gas effluent and, at the bottom a butadiene residue.

The term "solvent" means any polar solvent that is miscible in liquid phase with said butadiene feedstock under the operating conditions of said 1-butene separation section, having a volatility lower than that of the compounds 1,3-butadiene, 2-butene and butynes, so as to remain in the liquid phase in said 1-butene separation section, but being able to be separated from these compounds by distillation. Said solvent is advantageously chosen from the group constituted by dimethylformamide (DMF), N-methylpyrrolidone, acetonitrile, and mixtures thereof.

In the preferred case in which said solvent is DMF, since the water-DMF mixture is corrosive, the water content in the butadiene extract, which is advantageously compressed, must be adjusted in accordance with the metallurgical constraints. Furthermore, the corroded elements will have a tendency to catalyze the butadiene polymerization reaction, leading to a loss of yield and a risk of clogging of the lines. The water content may be reduced via any means known to those skilled in the art, for example by drying, advantageously by drying over an adsorbent, the adsorbent possibly being silica-based and/or alumina-based. In a non-limiting manner, this adsorbent may be a zeolite such as a zeolite 3A or 4A. Advantageously, the water content in the butadiene extract, which is advantageously compressed, is reduced to a value of less than 3% by weight of said effluent. It is also possible to add a corrosion inhibitor known to those skilled in the art to said effluent.

The light gaseous effluent produced at the top of the extractive distillation of said 1-butene separation section comprises 1- and 2-butenes and also light gases such as hydrogen, ethane, ethylene, propane and propylene. When the content of light gases in the butadiene extract, which is advantageously compressed, is high, for example greater than 2% of the total weight of said extract, substantial cooling of the top of said extractive distillation may be necessary in order to ensure a sufficient reflux in said column. This cooling is conventionally performed using a cold group.

The light gaseous effluent may be burnt to provide some of the heat required for the hot oil circuit or the steam boilers of the process.

Advantageously, said butadiene extract obtained from step c), which is advantageously compressed, is prewashed by placing in contact with a stream comprising a polar solvent chosen from the group constituted by dimethylformamide (DMF), N-methylpyrrolidone (NMP) and acetonitrile, prior to being fed into said 1-butene separation section. This prewashing makes it possible to separate the majority of the light gases and thus to dispense with cooling requiring the use of a cold group at the top of said 1-butene separation section.

Said section for separating 1-butene by extractive distillation is operated so that said butadiene residue comprises at least 95% by weight, advantageously at least 98% by weight and preferably at least 99% by weight of the butadiene included in said butadiene extract, which is advantageously compressed. Said section is also operated such that the amount of 1-butene in said butadiene residue represents not more than 0.5% of the weight of butadiene included in said residue. The operation is performed by adjusting the ratio of the flow rate of solvent to the flow rate of butadiene effluent, and also the degree of reflux of the extractive distillation, as is known to those skilled in the art.

Said 1-butene separation section is operated at the lowest possible pressure to limit the exposure of the butadiene-rich streams to high temperatures at which polymerization or decomposition might take place. Preferably, the operating pressure of said section is less than 0.6 MPa and preferably less than 0.5 MPa.

Said step d) comprises a section for separating out the solvent by distillation fed with said butadiene residue obtained from the 1-butene separation section and separating at the top a topped butadiene distillate and at the bottom a solvent residue.

The distillation is advantageously a conventional distillation known to those skilled in the art, performed such that said solvent residue comprises less than 1% by weight of butadiene, and advantageously no longer comprises any butadiene, and such that said topped butadiene distillate comprises less than 0.5% by weight of solvent, and advantageously no longer comprises any solvent.

Said distillation is advantageously operated at the lowest possible pressure to limit the exposure of the butadiene-rich streams to high temperatures at which polymerization or decomposition might take place. Said distillation is advantageously operated at a head temperature of less than 60° C., preferably less than 50° C., and at a head pressure of less than 0.5 MPa, preferably less than 0.4 MPa.

Said solvent residue advantageously feeds the 1-butene separation section as a stream comprising a solvent, advantageously as a mixture with a supply of solvent.

Said step d) comprises a final distillation section fed with the topped butadiene distillate obtained from the solvent separation section, separating at the top a purified butadiene effluent and at the bottom a butene residue.

This section makes it possible to remove the heavy impurities, and especially the traces of cis-2-butenes, and also the residual 1-butynes and the 1,2-butadiene and diethyl ether that may be present in the topped butadiene distillate.

Said purified butadiene effluent comprises at least 99.5% by weight of butadiene. The yield for the purification step d) according to the invention, defined as the flow rate of butadiene in the purified butadiene effluent over the flow rate of butadiene in the butadiene extract, which is advantageously compressed, feeding step d) is at least equal to 95% by weight, preferably to 98%, preferably greater than 99% by weight.

The alkynes containing 4 carbon atoms, which may be present in the topped butadiene distillate feeding said final distillation section, are separated in the purified butadiene effluent. If the final distillation does not make it possible to separate the alkynes containing 4 carbon atoms, which may be present in the topped butadiene distillate, so that their content in said purified butadiene effluent meets the specifications required for a subsequent use of said effluent, said topped butadiene distillate is advantageously treated, prior to being fed into said final distillation section, in a second extractive distillation section.

Said second extractive distillation section is fed with said topped butadiene distillate and with a stream comprising a solvent and produces at the top the topped butadiene distillate feeding the final distillation section and at the bottom a spent solvent residue comprising the solvent and, depending on their presence, alkynes containing 4 carbon atoms.

Said solvent is advantageously chosen from the group constituted by dimethylformamide (DMF), N-methylpyrrolidone (NMP) and acetonitrile.

Said second extractive distillation section is operated such that said topped butadiene distillate feeding the final distillation section comprises at least 98% by weight, advantageously at least 99% by weight of the butadiene included in said butadiene distillate feeding said second extractive distillation section. Said section is also operated such that the content of alkynes containing 4 carbon atoms present in the purified butadiene effluent at the top of the final distillation section complies with the specifications required for the subsequent use of said effluent. The operation is performed by adjusting the ratio of the flow rate of solvent to the flow rate of topped butadiene distillate, and also the degree of reflux of said extractive distillation section, as is known to those skilled in the art.

Said second extractive distillation section is operated at the lowest possible pressure to limit the exposure of the butadiene-loaded streams to high temperatures at which polymerization or decomposition might take place. Preferably, the operating pressure of said section is less than 0.6 MPa and preferably less than 0.5 MPa.

In the particular arrangement in which a second extractive distillation section is used, said spent solvent residue feeds a second section for separating out the solvent by distillation, separating at the top a distillate of alkynes containing 4 carbon atoms and at the bottom a solvent residue.

The distillation is a conventional distillation known to those skilled in the art, operated such that said solvent residue comprises less than 1% by weight of butadiene, and advantageously no longer comprises any butadiene, and such that the loss of solvent in said distillate of alkynes containing 4 carbon atoms is less than 0.05% by weight, preferably less than 0.01% by weight. The term "loss of solvent" means the ratio of the flow rate of solvent in said distillate of alkynes containing 4 carbon atoms to the flow rate of solvent in said spent solvent residue.

Said distillation is also operated such that the content of acetylenic compounds in said distillate of alkynes containing 4 carbon atoms does not exceed 30% by weight to avoid any risk of explosion promoted by an increase in the pressure and the temperature, this phenomenon being known to those skilled in the art.

Said distillation is advantageously operated at a head temperature of less than 60° C., preferably less than 50° C., and at a head pressure of less than 0.5 MPa, preferably less than 0.4 MPa.

Said solvent residue advantageously feeds the second extractive distillation section as a stream comprising a solvent, advantageously as a mixture with a supply of solvent.

The solvent residue obtained from the solvent separation section and the solvent residue obtained from the second solvent separation section may advantageously be mixed before feeding the 1-butene separation section and the second extractive distillation section. All or some of the solvent residue obtained from the solvent separation section and optionally from the second solvent separation section may advantageously be sent into a section for purification of the solvent, for example by distillation or any other operation known to those skilled in the art, to separate out the heavy impurities.

Effluent Treatment Step e)

The process according to the invention comprises an effluent treatment step e) fed with the spent water raffinate obtained from step e) and with the polluted reagent residue obtained from step b) and producing at least one ethanol-acetaldehyde effluent, an ethanol-water effluent and one or more brown oil effluents, preferably a light brown oil effluent and a heavy brown oil effluent.

Preferably, said step e) comprises at least a washing/backwashing section, a section for distilling the light brown oils, a section for distilling the heavy brown oils and an acetaldehyde separation section.

Said preferential washing/backwashing section is fed at an intermediate point with said polluted reagent residue obtained from step b).

Said preferential washing/backwashing section is fed at the bottom with a hydrocarbon effluent and the top with at least a fraction of the spent water raffinate obtained from step c). The hydrocarbon effluent and the spent water raffinate fraction obtained from step c) are fed at a temperature preferably between 10 and 70° C., preferentially between 45 and 55° C. Said washing/backwashing section produces at the top a washing hydrocarbon extract charged with a fraction of the impurities and of the brown oils, and at the bottom an ethanol/acetaldehyde/water raffinate.

Said washing/backwashing section is preferably operated at a pressure of between 0.1 and 0.5 MPa, preferentially between 0.2 and 0.4 MPa. Preferably, the addition of water to perform the backwashing is such that the water content in the water/ethanol/acetaldehyde raffinate is greater than 30% by weight, preferably greater than 40% by weight.

In one embodiment, the contact between the two liquid phases in said washing/backwashing section takes place in a liquid-liquid extractor. Various contact methods may be envisaged. Mention may be made, in a non-limiting manner, of a packed column, a pulsed column, or a stirred compartmented column. In another embodiment, the contact between the two liquid phases in said washing/backwashing section takes place in a membrane contactor, or a cascade of membrane contactors. This contact method is particularly well suited to the system used. Specifically, water-ethanol-hydrocarbon mixtures are known to form stable emulsions, which may be problematic in a liquid-liquid extractor. The membrane contactor makes it possible to generate a substantial area of contact, promoting the transfer of the impurities and oils to the hydrocarbon phase, without generating an emulsion.

The processes of the prior art propose backwashing with a recycled stream of water. Now, the Applicant has discovered that the backwashing operation is more efficient with water containing only very little acetaldehyde and butadiene than with a recycled water which may be polluted with liquid impurities, and this being the case without increasing the total flow rate of water either entering or leaving the process.

The use of the spent water raffinate obtained from step c) limits the accumulation of impurities when compared with the prior art processes. Furthermore, the injection of the ethanol feedstock into the water-ethanol separation section and its non-use for washing the reaction effluent limits the ethanol concentration in the circulation loops of the effluent treatment step e), thus limiting the reactions between ethanol and acetaldehyde in the washing/backwashing section, which limits the losses in the form of hemi- and diethyl acetal, without having a negative impact on the functioning of the light and heavy brown oil distillation sections.

Said washing hydrocarbon extract feeds said light brown oil distillation section, which produces as distillate said light brown oil effluent, and a hydrocarbon residue comprising the heavy fraction of the brown oils.

Said light brown oil effluent is composed of impurities produced in the reaction section of step a), mainly diethyl ether, ethyl acetate and crotonaldehyde, and also of the light fraction of the brown oils, composed of impurities in smaller amount, among which are pentene, isoprene, butanal and vinyl ethyl ether. This effluent may be burnt to provide some of the heat required for the hot oil circuit or for the steam boilers of the process, or distilled to recover a diethyl ether effluent and/or an ethyl acetate/crotonaldehyde effluent, which may either be upgraded, or recycled into the reaction section of step a) to be retransformed.

Said hydrocarbon residue essentially contains the hydrocarbons serving for washing, but also the heaviest fraction of the brown oils. To avoid accumulation of the brown oils by recycling of the hydrocarbon effluent into the liquid-liquid extractor, a fraction of said hydrocarbon residue is treated in said heavy oil distillation section, consisting of a distillation column, which produces a hydrocarbon distillate essentially composed of hydrocarbons with a few remaining traces of brown oils and, as residue, said heavy brown oil effluent comprising more than 80%, preferentially more than 85% of hydrocarbons and also the heaviest brown oils. The fraction of said hydrocarbon effluent sent to said oil distillation section is between 5% and 30% of the total flow of said hydrocarbon residue, and preferentially between 10% and 20%. The hydrocarbon distillate is mixed with the fraction of the hydrocarbon residue that has not been treated in said heavy oil distillation section so as to form the hydrocarbon effluent feeding said washing/backwashing section.

This effluent, which preferably represents between 0.1% and 20% of the feedstock of said heavy oil distillation section, preferentially between 0.3% and 5%, may be burnt to provide some of the heat required for the hot oil circuit or the steam boilers of the process. A supply of hydrocarbons equivalent to the losses at the bottom of said heavy oil distillation section is necessary to keep the washing flow rate constant. This column is adjusted so as to keep constant the concentration of brown oils in the hydrocarbon recycling loop (hydrocarbon effluent/washing hydrocarbon effluent loop).

The light and heavy brown oil effluents are removed from the process.

The polluted reagent residue obtained from step b) mainly comprises ethanol, acetaldehyde and water, but also impurities such as diethyl ether, ethyl acetate and the brown oils as defined previously. These impurities may accumulate if they are sent into step a) in the ethanol-acetaldehyde effluent and/or the water-ethanol effluent and if they are only partially converted in the reaction section of step a). The washing/backwashing section makes it possible to recover some of these impurities before the water-acetaldehyde separation section of step e) and the water-ethanol separation section of step a), which makes it possible to avoid the demixing of the brown oils in these sections.

The washing of the polluted reagent residue obtained from step b) with a hydrocarbon effluent entrains certain impurities, whereas the backwashing of the hydrocarbon stream with a fraction of the spent water residue obtained from step c) limits any loss of acetaldehyde and of ethanol.

Said hydrocarbon effluent may contain saturated and/or unsaturated and/or aromatic hydrocarbons, preferably saturated hydrocarbons. Said hydrocarbon effluent is advantageously constituted of a mixture of hydrocarbons containing between 6 and 40 carbon atoms, preferably between 10 and 20 carbon atoms. In a non-limiting manner, said hydrocarbon effluent may be a desulfurized gas oil or kerosene fraction or alternatively a hydrocarbon fraction produced by a unit of Fischer-Tropsch type.

The addition of water to the washing/backwashing section allows better functioning of the process for removing the impurities and brown oils according to the invention.

The process according to the invention thus avoids the regular purging of ethanol in order to avoid the accumulation of brown oils, which makes it possible to improve the overall performance of the process.

Said water/ethanol/acetaldehyde effluent obtained from the washing/backwashing section feeds said acetaldehyde separation section, in which the acetaldehyde is separated so as to form an ethanol-acetaldehyde effluent and an ethanol-water effluent.

The ethanol-acetaldehyde effluent obtained from step e) is predominantly constituted of acetaldehyde and ethanol. The term "predominantly" means that the ethanol+acetaldehyde combination represents more than 80% by weight, preferably more than 85% by weight of said effluent. In a non-limiting manner, the ethanol-acetaldehyde effluent obtained from step e) may contain impurities such as water, ethyl acetate or acetone. The impurities other than water represent less than 10% and preferentially less than 5% by weight of the stream.

In one embodiment of the invention, said ethanol-acetaldehyde effluent undergoes a purification step before being recycled into the rest of the process. The term "purification" means placing said effluent in contact with adsorbents, for instance active charcoal, silica, alumina or a functionalized polymeric resin.

DESCRIPTION OF THE FIGURES

FIG. 1 schematically shows a general view of the process according to the invention.

A step A for converting ethanol into butadiene is fed with an ethanol feedstock (1), and with the ethanol-water effluent (11) and with the ethanol-acetaldehyde effluent (10) obtained from step E. This step produces a reaction effluent (2) which feeds a distillation step B, which produces a butadiene distillate (3) and a polluted reagent residue (4).

The butadiene distillate (3) and a stream of water (5) feed step C of washing with water so as to produce a hydrated butadiene extract (6) and a spent water raffinate (7).

The hydrated butadiene extract (6) feeds the butadiene purification step D so as to be separated into a light gaseous effluent (8), a purified butadiene effluent (9), a solvent residue and a butene residue (these last two residues not being shown).

The effluent treatment step E is fed with the polluted reagent residue (4) obtained from step B and with the spent water raffinate (7) obtained from step C and produces an ethanol-acetaldehyde effluent (10), an ethanol-water effluent (11), a light brown oil effluent and a heavy brown oil effluent (these last two effluents not being shown).

EXAMPLES

The examples that follow are based on simulations integrating the recycling of the streams. In each of the examples, the flow rate of ethanol feedstock is adjusted so as to obtain an annual production of 150 kt/year of a purified butadiene effluent in a purity of between 99.5% and 100% by weight.

All the percentages are weight percentages.

Example 1—Comparative

A process for producing butadiene from ethanol in accordance with the process described in WO 2016/042095 is fed with 48.2 t/h of an ethanol feedstock comprising 93.4% by weight of ethanol. This scheme does not involve extractive distillation and the ethanol feedstock is used to wash the reaction effluent.

The ethanol feedstock is used to wash the vapour effluent obtained from the reaction section, after which said vapour effluent was separated from its liquid part and compressed.

The ethanol feedstock obtained from the washing section is mixed with the liquid part of the effluent from the reaction section, forming a stream of 166 t/h comprising 54% ethanol, 4% acetaldehyde, 23% water and 11% butadiene.

This stream is treated in a distillation section producing at the top 20 t/h of a distillate comprising butadiene and 146 t/h of a residue no longer comprising any butadiene, and comprising 61% ethanol, 4% acetaldehyde and 27% water.

The distillate comprising the butadiene is successively treated by washing with water, drying, cryogenic distillation and separation with DMSO so as to produce 18.75 t/h of a purified butadiene effluent comprising 99.6% butadiene. The washing with water uses 21 t/h of water originating from outside the process. The water obtained from the washing of the distillate comprising the butadiene feeds the acetaldehyde separation section.

The vapour effluent washed with the ethanol feedstock is washed with water obtained from the effluent treatment so as to take up the traces of ethanol and acetaldehyde. The water obtained from this washing (about 0.4 t/h) feeds a water-ethanol separation section.

The 146 t/h of residue are treated in a washing/backwashing section with hydrocarbons so as to separate out the impurities, and in particular the brown oils. The effluent from this section, representing 168 t/h and comprising 53% ethanol, 4% acetaldehyde and 40% water, feeds two distillation columns making it possible to separate an ethanol-acetaldehyde effluent, an ethanol effluent and a water effluent, which is partly (29.5 t/h) recycled into the washing of the vapour effluent obtained from the reaction section (0.4 t/h) and into the washing/backwashing section (29.1 t/h), and partly (41.4 t/h) purged.

The ethanol effluent (95.7 t/h comprising 79% ethanol) and the ethanol-acetaldehyde effluent (23.2 t/h comprising 57% ethanol and 27% acetaldehyde) feed the reaction section.

The energy consumption of this scheme in terms of utilities (electricity, gas and steam) expressed in MWh is 178.8 MWh.

Example 2—in Accordance with the Invention

A process for producing butadiene from ethanol in accordance with the process according to the invention is fed with 48.2 t/h of an ethanol feedstock comprising 93.4% by weight of ethanol.

In accordance with the invention, the ethanol feedstock is not used to wash the vapour effluent obtained from the reaction section. The ethanol feedstock is fed into the top of the ethanol-water separation section, which separation is performed in a distillation column. This separation section produces at the bottom 41.3 t/h of water which is purged from the process, and at the top 90 t/h of ethanol effluent feeding the reaction section.

The reaction section comprises two reaction zones. The first is fed with 75 t/h of the ethanol effluent. The effluent from the first reaction zone is separated into a gaseous effluent and a liquid effluent. The gaseous effluent (about 11 t/h) is washed with the 15 t/h of the ethanol effluent not feeding the first reaction zone. The washed gas (1 t/h) mainly comprises hydrogen. The ethanol effluent which has washed the gaseous effluent, as a mixture with the liquid effluent and the ethanol-acetaldehyde effluent obtained from the effluent treatment step, feeds the second reaction zone at a total flow rate of 112 t/h.

The reaction effluent obtained from the second reaction zone forms a 112 t/h stream comprising 39% ethanol, 6% acetaldehyde, 28% water and 17% butadiene.

This stream is treated in a distillation section producing at the top 20 t/h of a distillate comprising butadiene and 91.5 t/h of a residue no longer comprising any butadiene, and comprising 48% ethanol, 7% acetaldehyde and 34% water.

The distillate comprising the butadiene is successively treated by washing with water and drying, before being fed into a step for purifying butadiene by extractive distillation so as to produce 18.75 t/h of a purified butadiene effluent comprising 99.6% butadiene. The washing with water uses 21 t/h of water originating from outside the process. The water obtained from the washing of the distillate comprising butadiene is fed into the top of the section for the washing/backwashing with hydrocarbons of the effluent treatment step (in the example not in accordance, this water feeds the acetaldehyde separation section).

The 91.5 t/h of residue no longer comprising any butadiene feed, at an intermediate point, a section for washing/backwashing with hydrocarbons in an effluent treatment step so as to separate out the impurities, and in particular the brown oils. The effluent from this section, representing 106 t/h and comprising 41% ethanol, 6% acetaldehyde and 49% water, feeds an acetaldehyde separation section making it possible to separate an ethanol-acetaldehyde effluent and an ethanol-water effluent. The ethanol-acetaldehyde effluent (23.3 t/h comprising 56% ethanol and 27% acetaldehyde) feeds the second reaction zone.

The ethanol-water effluent feeds the ethanol-water separation section at an intermediate point, this section moreover being fed at the top with the ethanol feedstock as indicated at the start of the example.

Relative to the process not in accordance, a similar overall butadiene yield is obtained (same flow rate of purified butadiene effluent for the same flow rate of feedstock).

The energy consumption of this scheme in terms of utilities (electricity, gas and steam) expressed in MWh is 146.3 MWh, i.e. an 18% reduction in the consumption of utilities. This saving is partly due to better management of the water circuit. The reduction in the flow of water circulating in the process leads to a reduction in consumption as regards the separation operations. The choice of the point of injection of the ethanol feedstock also lightens the workload of the separation operations. Since the ethanol feedstock is no longer used for washing the reaction effluents, it is no longer treated in the effluent treatment steps. These reductions in flow therefore also have the consequence of reducing the size of the equipment.

The invention claimed is:

1. Process for producing butadiene from an ethanol feedstock comprising at least 80% by weight of ethanol, said process comprising:
    a) a step for converting the ethanol into butadiene, comprising:
        a water-ethanol separation section fed with at least a fraction of said ethanol feedstock and with a fraction of the ethanol-water effluent obtained from step e) and producing an ethanol effluent and a purged water effluent;
        a reaction section fed with said ethanol effluent and operated at a pressure of between 0.1 and 1.0 MPa and at a temperature of between 200 and 500° C. in the presence of a catalyst and producing a reaction effluent;
    b) a distillation step fed with the reaction effluent obtained from step a) and producing a polluted reagent residue and a butadiene distillate, operated at a pressure of between 0.1 and 1 MPa;
    c) a step of washing with water comprising at least one gas-liquid washing section fed at the bottom with the butadiene distillate obtained from step b) and at the top with a stream of water, and producing at the top a hydrated butadiene extract and at the bottom a spent water raffinate;
    d) a butadiene purification step fed with the butadiene extract obtained from step c) and producing at least one light gas effluent and a purified butadiene effluent comprising at least:
        a section for separating the 1-butene by extractive distillation fed with said butadiene extract and with a stream comprising a solvent, separating at the top a light gas effluent and, at the bottom a butadiene residue;
        a section for separating out the solvent by distillation fed with said butadiene residue obtained from the 1-butene separation section and separating at the top a topped butadiene distillate and at the bottom a solvent residue;
        a final distillation section fed with the topped butadiene distillate obtained from the solvent separation section, separating at the top a purified butadiene effluent and at the bottom a butene residue;
    e) an effluent treatment step fed with the spent water raffinate obtained from step c) and with the polluted reagent residue obtained from step b) and producing at least one ethanol-acetaldehyde effluent, an ethanol-water effluent and one or more brown oil effluents.

2. Process according to claim 1, wherein said water-ethanol separation section of said step a) is operated by distillation.

3. Process according to claim 1, wherein the ethanol effluent obtained from the water-ethanol separation section of step a) undergoes a purification step before being fed into the reaction section.

4. Process according to claim 1, wherein said reaction section of said step a) comprises two reaction zones, the first fed with a fraction of said ethanol effluent and optionally a part of said ethanol feedstock, and the second fed with the effluent from the first reaction zone, with the residual fraction of said ethanol effluent and with a fraction of the ethanol-acetaldehyde effluent obtained from step e) and optionally with a part of said ethanol feedstock, the ethanol/acetaldehyde mole ratio at the inlet of said second reaction zone being between 1 and 5.

5. Process according to claim 4, wherein a gas-liquid separation means is used between the two reaction zones to separate the effluent from the first reaction zone into a gaseous effluent and a liquid effluent, the liquid effluent feeding the second reaction zone.

6. Process according to claim 1, wherein the reaction effluent obtained from step a) undergoes a gas-liquid separation before feeding step b) consisting in cooling the reaction effluent obtained from step a) to a temperature of between 10 and 100° C. and to obtain, in a gas/liquid separator, at least one liquid effluent and at least one vapour effluent, the vapour effluent feeding the distillation step b) as reaction effluent obtained from step a), the liquid effluent feeding the effluent treatment step e).

7. Process according to claim 1, wherein the hydrated butadiene extract obtained from step c) is compressed to a pressure of between 0.1 and 1.0 MPa.

8. Process according to claim 1, wherein the solvent of said 1-butene separation section of said step d) is chosen from the group constituted by dimethylformamide, N-methylpyrrolidone and acetonitrile, and mixtures thereof.

9. Process according to claim 1, wherein said butadiene extract obtained from step c) is prewashed by placing in contact with a stream comprising a polar solvent chosen from the group constituted by dimethylformamide (DMF), N-methylpyrrolidone (NMP) and acetonitrile, prior to being fed into said 1-butene separation section.

10. Process according to claim 1, wherein said solvent residue from the solvent separation section of step d) feeds the 1-butene separation section of step d) as a stream comprising a solvent.

11. Process according to claim 1, wherein the topped butadiene distillate is treated, prior to being fed into the final distillation section of step d), in a second extractive distillation section, said second extractive distillation section being fed with said topped butadiene distillate and with a stream comprising a solvent and producing at the top the topped butadiene distillate feeding the final distillation section of step d), and at the bottom a spent solvent residue, said spent solvent residue feeding a second section for separating out the solvent by distillation, separating at the top a distillate of alkynes containing 4 carbon atoms and at the bottom a solvent residue.

12. Process according to claim 11, wherein said solvent residue obtained from the second solvent separation section feeds the second extractive distillation section as a stream comprising a solvent.

13. Process according to claim 12, wherein the solvent residue obtained from the solvent separation section and the solvent residue obtained from the second solvent separation section are mixed before feeding the 1-butene separation section and the second extractive distillation section.

\* \* \* \* \*